United States Patent

Goto et al.

[11] Patent Number: 5,430,475
[45] Date of Patent: Jul. 4, 1995

[54] ELECTRONIC ENDOSCOPE APPARATUS HAVING MICRO ARRAY ON PHOTOELECTRIC CONVERSION SURFACE

[75] Inventors: Masahito Goto, Hachioji; Kiyoshi Tsuji, Musashino; Akira Hasegawa, Mitaka; Mitsunobu Ono, Suginami; Akibumi Ishikawa, Hachioji, all of Japan

[73] Assignee: Olympus Optical Co., Ltd., Tokyo, Japan

[21] Appl. No.: 338,198

[22] Filed: Nov. 9, 1994

Related U.S. Application Data

[63] Continuation of Ser. No. 96,826, Jul. 26, 1993, abandoned, which is a continuation of Ser. No. 665,866, Mar. 7, 1991, abandoned.

[30] Foreign Application Priority Data

Jun. 29, 1990 [JP] Japan ................ 2-174039
Dec. 21, 1990 [JP] Japan ................ 2-405221

[51] Int. Cl.⁶ .............................. H04N 7/18
[52] U.S. Cl. ............................... 348/65; 348/68; 348/73
[58] Field of Search ........... 359/619, 626; 348/65, 348/71, 73, 68

[56] References Cited

U.S. PATENT DOCUMENTS

| | | | |
|---|---|---|---|
| 4,082,451 | 4/1978 | Patel | 359/626 |
| 4,694,185 | 9/1987 | Weiss | 358/213.11 |
| 5,001,556 | 3/1991 | Nakamura et al. | 358/98 |
| 5,088,492 | 2/1992 | Takayama et al. | 358/98 |

*Primary Examiner*—Curtis Kuntz
*Assistant Examiner*—Minsun Oh
*Attorney, Agent, or Firm*—Armstrong, Westerman, Hattori, McLeland & Naughton

[57] ABSTRACT

The arrangement of a converging light device array wherein each converging light device increasing a quantity of incident light entering every one or more photoelectric conversion pixel is arranged in front of a photoelectric conversion surface of a solid state imaging device photoelectrically converting an optical image based on an objective optical system substantially ensures that an aperture area of the photoelectric conversion pixel enlarges and the sensitivity improves.

21 Claims, 12 Drawing Sheets

FIG. 4 *(PRIOR ART)*
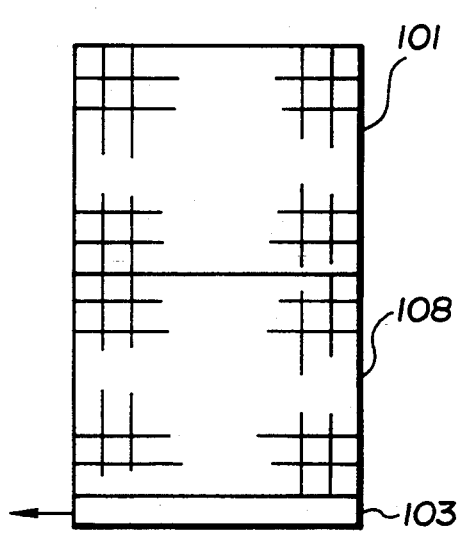
FIG. 5 *(PRIOR ART)*
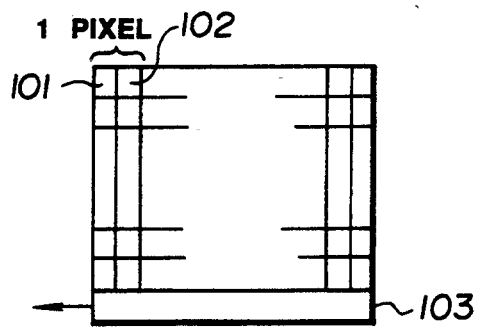
FIG. 6 *(PRIOR ART)*
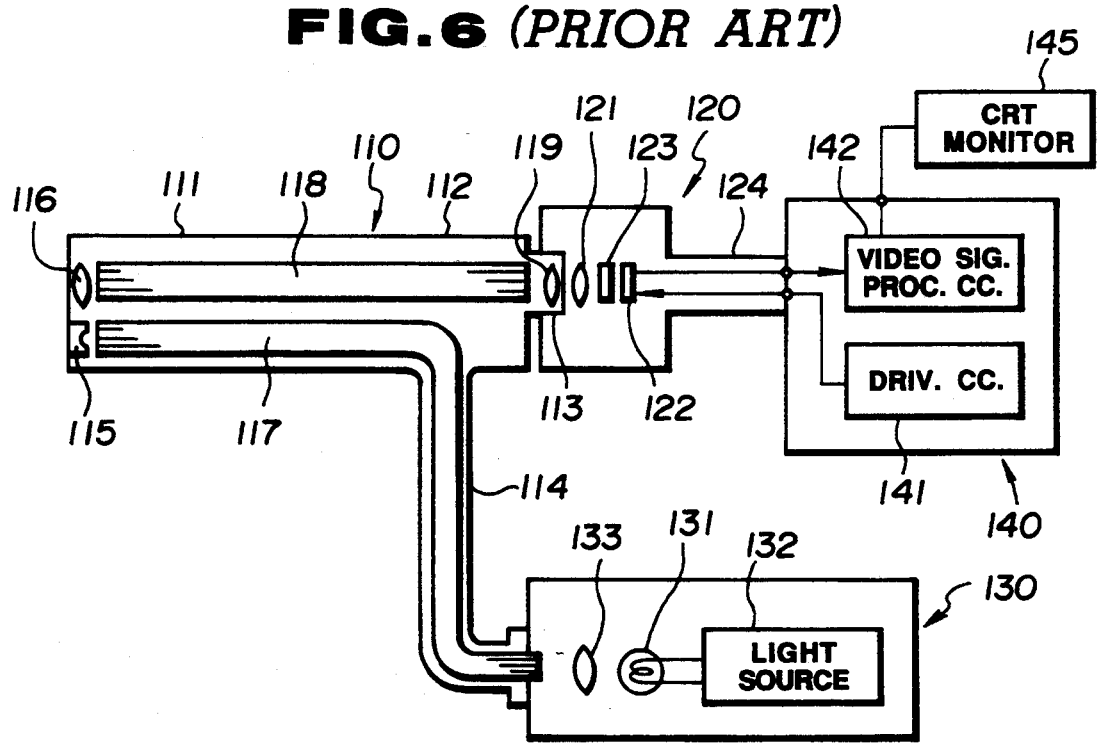

TS

VS

HS

ELECTRONIC ENDOSCOPE APPARATUS HAVING MICRO ARRAY ON PHOTOELECTRIC CONVERSION SURFACE

This application is a continuation of application Ser. No. 08/096,826 filed Jul. 26, 1994, now abandoned, which is a continuation of application Ser. No. 07/665,866 filed Mar. 7, 1991, now abandoned.

BACKGROUND OF THE INVENTION

FIELD OF THE INVENTION AND RELATED ART STATEMENT

The present invention relates to an electronic endoscope apparatus having a micro lens array on a photoelectric conversion surface of a solid state imaging device which converts a subject image into electric signals.

Recently, there has come into use of an electronic endoscope (which is also called electronic scope) which has a solid state imaging device such as a charge coupled device (CCD) within the tip part of the endoscope insertion part to take a picture image of a subject. Such an electronic endoscope is connected to a video processor through a connector and various kinds of picture processing are applied to video signals so that a picture image of the subject is displayed on a CRT monitor. On the other hand, by using a fiberscope which has been existent so far and connecting a television camera (TV camera) to an eyepiece part of the fiberscope, a type of electronic endoscope apparatus fitting a TV camera outside whereby a picture image of a subject is displayed on a CRT monitor is also used. The TV camera picks up an optical image of a subject transferred to the eyepiece part through an image guide fiber within the fiberscope.

The performance of an electronic endoscope which composes the electronic endoscope apparatus is required having an efficient solid state imaging device, especially having many pixels and being highly sensitive. However, for example, in a medical endoscope, a diameter of a tip part of an insertion part cannot be wider because the medical endoscope is inserted into a narrow tube cavity or the body cavity. Also, in an endoscope system wherein a TV camera is connected to an eyepiece part of a fiberscope, since an optical image is transferred to the eyepiece part through an image guide fiber, the quantity of light of an optical image which enters an imaging part of the TV camera is attenuated or sensitivity is lowered or interference moire is generated by a pitch of a fiber and a pitch of a pixel of a solid state imaging device so that it has been necessary to insert an optical filter in an observing optical path.

As mentioned above, the solid state imaging device provided within the tip part of the endoscope insertion part is assigned a requirement of highly efficient pixel and smaller size which are contrary to each other. In order to make the solid state imaging device smaller while its high sensitivity is maintained, it is considered that a line transfer type CCD wherein a sensor part (light sensitive part) 101 and a vertical transfer part (V.CCD, hereinafter) 102 are combined as shown in FIG. 1 is the most suitable one. Also, a horizontal transfer resistor 103 is provided on one end of the sensor part 101 (and V.CCD 102). In this line transfer type CCD, because a smear ring is generated when an accident light enters at the charge transferring time, it is necessary to shield the light to prevent the smear ring.

Where the line transfer type CCD is used in the electronic endoscope apparatus, an exposure period and a shielding light period are alternately provided as shown in FIG. 2 so as to store a charge during the exposure period and transfer the charge and read it during the shielding light period.

Also, recently, a measure, that is, a treatment under an endoscope by laser beams or the like has been required for an endoscope examination. Both of the laser beams (invisible light) and visible lights are continuous, therefore, in an electronic endoscope apparatus using a line transfer type CCD, severe blooming phenomenon is caused by incident laser beams or visible guilding lights during a charge transferring period of the CCD so that the quality of a picture has been badly damaged and that a fine treatment in details has been affected. FIG. 3 shows an example of an endoscope picture image during the laser beams application in the electronic endoscope apparatus using the line transfer type CCD. As shown in FIG. 3, if laser beams 106 emanated from a laser probe 105 is applied to an affected part 104, a blooming 107 is generated in a neighboring part of the part applied by the laser beams 106.

Then, it is considered to use a system in which shielding is not needed, for example, a frame storage type (it is also called a frame transfer type) CCD or an interline type CCD. In the frame storage type CCD, a sensor part 101 and a storing part 108 are separately arranged as shown in FIG. 4 and a horizontal transmission resistor 103 is provided on one end of the storing part 108, which is the opposite side of the sensor part 101. On the other hand, in the interline type CCD, the sensor part 101 is arranged being adjacent to the V. CCD 102 as shown in FIG. 5.

In the frame storage type CCD, the storing part 108 is needed in addition to the sensor part 101 as mentioned above and there is a problem in which a tip part size becomes larger when an electronic endoscope having a solid state imaging device at the tip of the insertion part is used. Also, in the interline type CCD, if it is compared with the line transfer type or the frame storage type by a pixel of the same size, the size of the sensor part 101 is reduced by about half because a sensor device (sensitivity device) part 101 and a pixel part of a V. CCD part 102 which is adjacent to the sensor device part 101 compose one pixel as shown in FIG. 5 so that there is a problem in which an aperture ratio is lowered and the sensitivity is reduced by half.

An outside fitting electronic endoscope in which a TV camera 120 fitted outside is connected to an eyepiece part 113 of a fiberscope 110 is constructed, for example, as shown in FIG. That is, the fiberscope 110 comprises an insertion part 111, an operating part 112 fitted to the rear end of this insertion part 111, the eyepiece part 113 provided at the rear end of this operating part and a light guide cable 14 extended from the operating part 112. A luminous intensity distributing lens 115 and an objective lens 116 are provided at the tip part of the insertion part 111. A light guide fiber 117 is fitted to the rear end of the luminous intensity distributing lens 115. This light guide fiber 117 is inserted into the insertion part 111, the operating part 112 and the light guide cable 114 and an incident end part is connected to a light source apparatus 130. This light source apparatus 130 comprises a lamp 131, a power source 132 supplying power to this lamp 131 and a lens 133 converging light emanated from the lamp 131 and making the light enter the incident end of the light guide fiber 117. Also, a tip surface of an image guide fiber 118 is placed in an image forming position of the objective lens 116. This image guide fiber 118 is inserted into the insertion part 1 and the operating part 112 and the rear end surface of the image guide fiber 118 is opposed to an eyepiece lens 119 within the eyepiece part 113.

The TV camera 20 comprises an image forming optical system 121 which forms an image observed by the eyepiece part 113, a CCD 122 arranged in the image forming position of this image forming optical system 121 and an optical crystal low pass filter (LPF, hereinafter) 123 arranged on the observing optical path which leads to this CCD 122. The TV camera 120 is connected to a video processor 140 through a cable 124. This video processor 140 comprises a driving circuit 141 connected to the CCD 122 through a signal line inserted into the cable 124 and a video signal processing circuit 142. The CCD 122 is driven by the driving circuit 141 and an output signal of the CCD 122 is processed at the video signal processing circuit 142. Then, a video signal from the video signal processing circuit 142 is supplied to a CRT monitor 145 on which a subject image is displayed.

This outside fitting electronic endoscope has a problem in which moire stripes (false signals) are generated because of a spatial sampling of the CCD 122 for a pitch of each fiber of the image guide fiber 118. Also, if the interline type CCD is used as the CCD 122, the sizes of an aperture part (sensor part 101) and a shielding light part (V.CCD 102) fitted to the aperture part become a pitch P of an unit pixel of the spatial sampling as shown in FIG. 7. As a counterplan for the moire, the LPF 123 is inserted in the observing path so as to reduce the moire phenomenon under existing circumstances. As shown in FIG. 8, each fiber 151 of the image guide fiber 118 is arranged, and for example, all fibers are symmetrically arranged about the dark shading fiber in this diagram. Up to the present, sampling turning back distortion has been removed by a crystal filter as the LPF in the spatial direction of at least (1)-(4) in FIG. 8 in order to remove the moire. Also, in FIG. 8, P1 is a pitch of the image guide fiber 118 in the direction (1). In this case, the number of crystal filters which is the same number of the direction desired to be removed is needed and it amounts to four to six. The necessary thickness of each crystal filter t(mm) is 0.17×P1 in thickness for the pitch of the fiber P (mm) in the direction desired to be removed. As shown in FIG. 9, the LPF 123 consists of six filters has more than (10) mm in thickness and it was a big defect in its size, weight and price. Especially, in the TV camera 120 fitted outside of an endoscope, since a doctor keeps holding the TV camera during the medical examination and treatment, the increase in size and weight of the TV camera was a big weak point. Further, the high price of the six filters' composition makes the product costs higher.

Another method for removing the moire is to use a soft focusing lens utilizing spherical aberration as stated in Japanese Patent application No. 115107 of 1990 which was applied by the assignee. In this case, as shown in FIG. 10, at the same time that a modulation transfer function MTF falls as shown by the broken line, the threshold resolution also falls as compared with the case in which a soft focusing lens is not used as shown by the solid line. Also, FIG. 10 shows the MTF attached the condition of the pitch P of the unit pixel in the sampling in FIG. 7.

OBJECT AND SUMMARY OF THE INVENTION

An object of this invention is to provide an electronic endoscope apparatus wherein a highly sensitive picture quality can be obtained while using a small solid state imaging device.

Another object of this invention is to provide an electronic endoscope apparatus wherein moire can be reduced without using a low pass filter.

In an electronic endoscope comprising a solid state imaging device as an imaging means, the electronic endoscope apparatus of this invention increases an effective aperture ratio by fitting a condenser device array in which condenser devices increasing the quantity of light entering every pixel of a predetermined number, such as an unit pixel are arranged in front of a photoelectric conversion surface of the solid state imaging device so that sensitivity can be improved and moire can be reduced.

BRIEF DESCRIPTION OF DRAWINGS

FIG. 4 is an illustration showing a frame storage type CCD.

FIG. 5 is an illustration showing an interline type CCD.

FIG. 6 is an illustration showing an example of an electronic endoscope apparatus fitting a TV camera outside.

FIG. 12 is an illustration showing an outline of an electronic endoscope apparatus.

FIG. 16 is an illustration showing the structure of a main part of a CCD.

FIG. 17 is a characteristic diagram showing a change of MTF accompanied by a change of an aperture ratio.

FIG. 19 is an illustration showing the structure of a main part of a CCD of the third embodiment.

FIG. 24b is a sectional view of FIG. 24a.

DETAILED DESCRIPTION OF THE PREFERRED EMBODIMENTS

Figure 1:
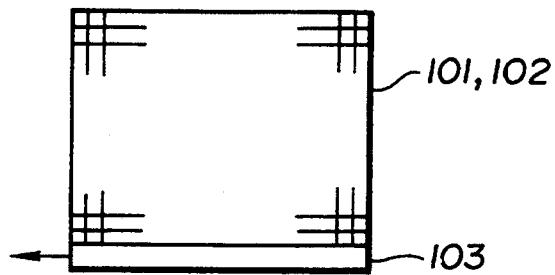
FIG. 1 is an illustration showing a line transmission type CCD.
Figure 2:
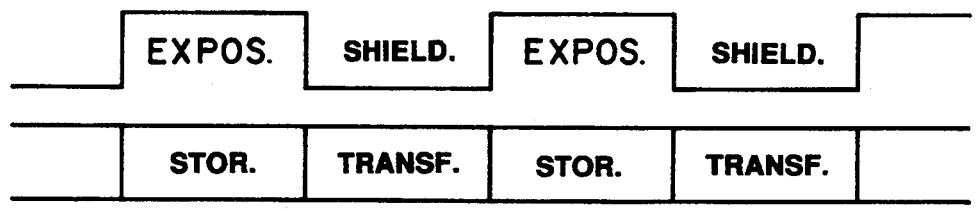
FIG. 2 is an illustration showing an operation of a line transfer type CCD.
Figure 3:
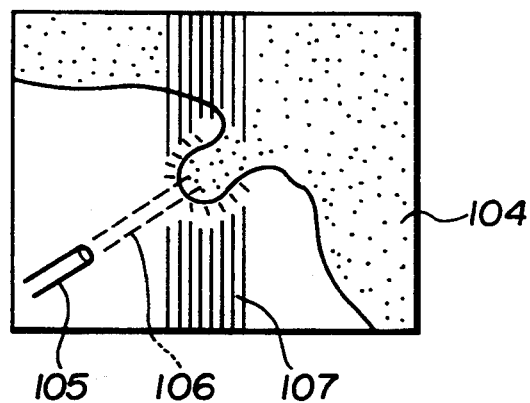
FIG. 3 is an illustration showing an example of an endoscope picture image during the application of laser beams in an electronic endoscope apparatus using a line transfer type CCD.
Figure 7:
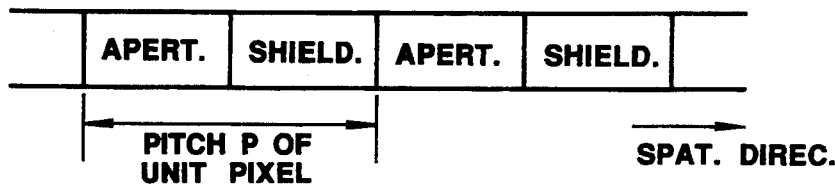
FIG. 7 is an illustration showing a pitch of an unit pixel in an interline type CCD.
Figure 8:
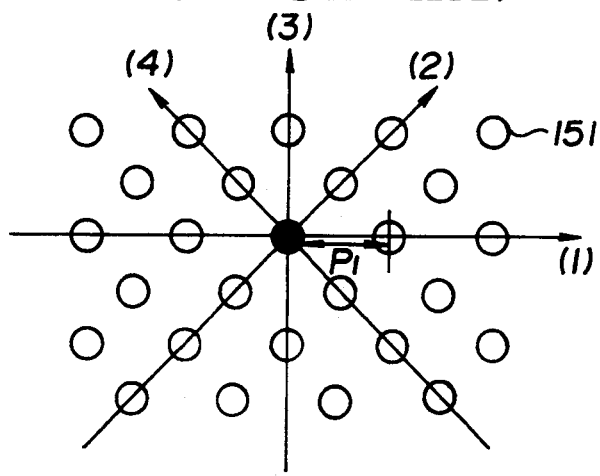
FIG. 8 is an illustration showing an arrangement of each fiber of an image guide fibers.
Figure 9:
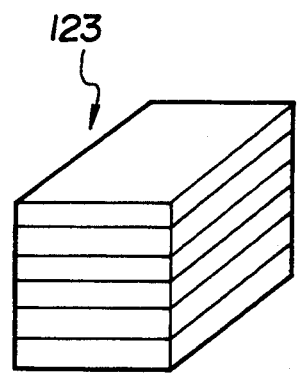
FIG. 9 is a perspective view showing a low pass filter using a crystal filter.
Figure 10:
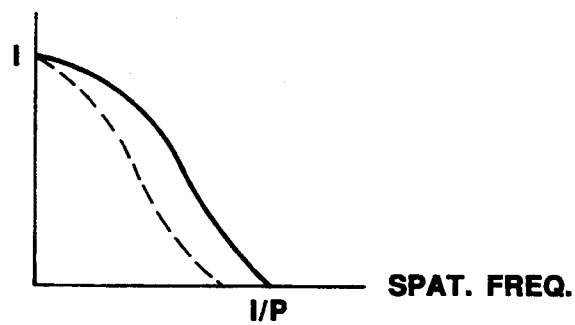
FIG. 10 is a characteristic diagram showing a modulation transfer characteristic in related art.
Figure 11:
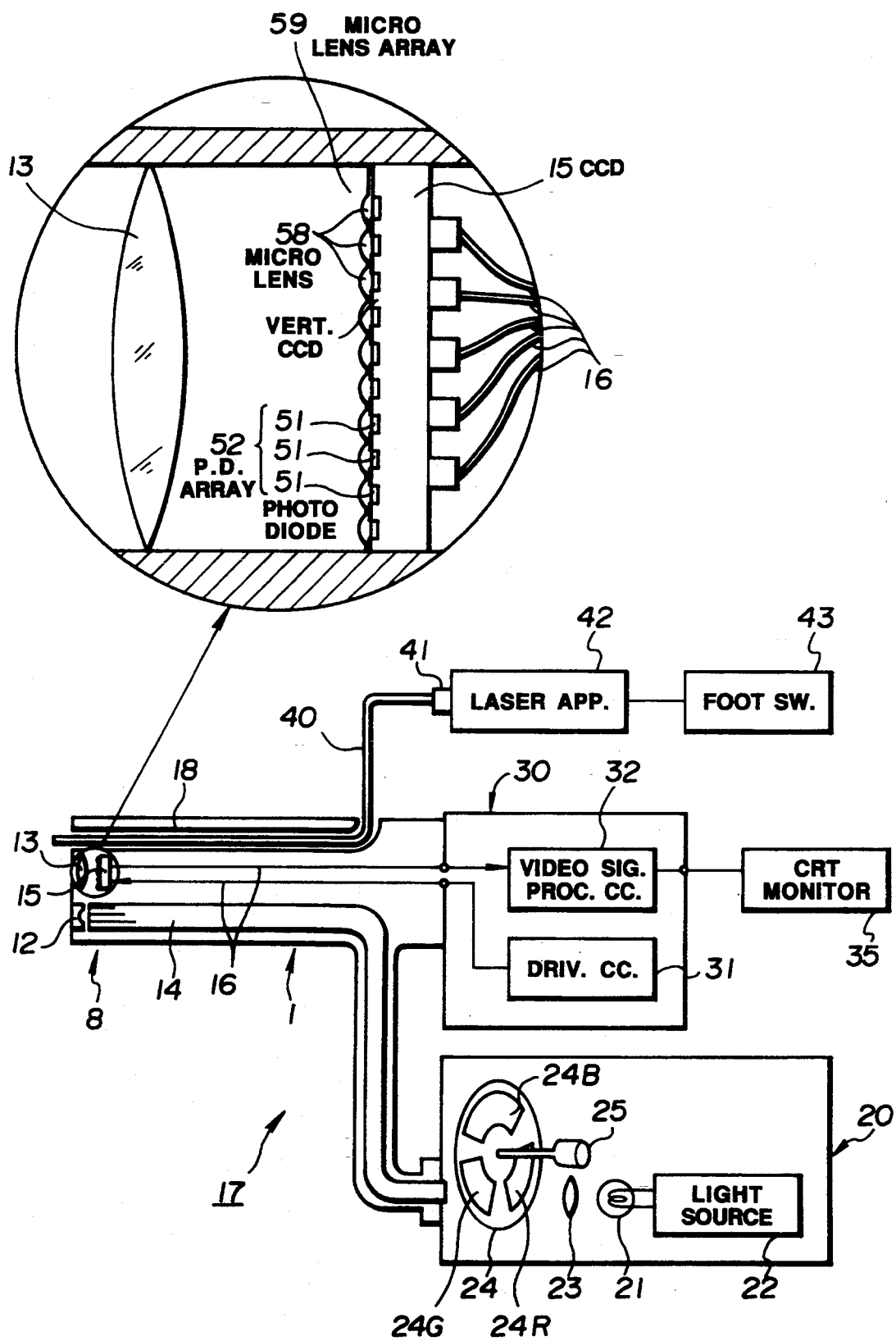
FIGS. 11 to 13 relates to the first embodiment of this invention and FIG. 11 is an illustration showing the whole structure of an electronic endoscope apparatus of the first embodiment.
Figure 12:
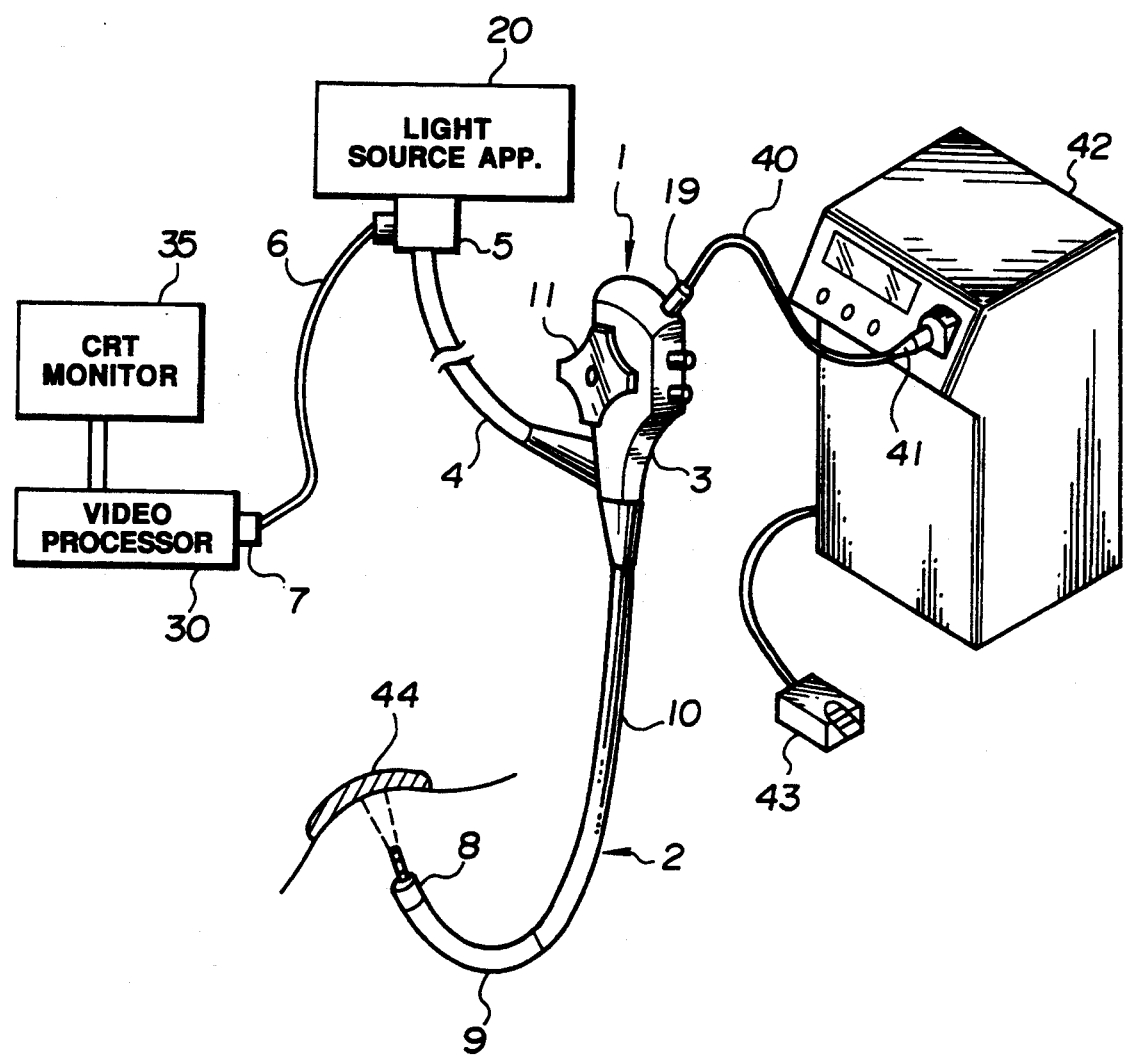

As shown in FIGS. 11 and 12, an electronic endoscope apparatus 17 of the first embodiment of this invention comprises an electronic endoscope 1 having an imaging means and an illuminating light transmitting means within, a video processor 30 processing a signal for a light source apparatus 20 supplying an illuminating light to (the illuminating light transferring means of) this electronic endoscope 1 and the imaging means, and a CRT monitor 35 which is connected to the video processor 30 and displays a video signal.

As shown in FIG. 12, the electronic endoscope 1 comprises an elongated flexible insertion part 2, an operating part 3 fitted to the rear end (proximal end) of this insertion part 2, an universal cord 4 extended from the side part of this operating part 3, a light source connector 5 provided at the end part of this universal cord 4 and removably connected to the light source apparatus 20, an electric cable 6 extended from this light source connector 5, and an electric connector 7 provided at the end part of this electric cable 8 and removably connected to a connector receiver of the video processor 30.

The insertion part 2 is composed of, in order from the tip (terminal end) side, a rigid tip part 8, a bendable bending part 9 and a flexible part 10. Also, a bending operation knob 11 for bending and operating the bending part 9 is provided on the operating part 3.

As shown in FIG. 11, a luminous intensity distributing lens 12 and an objective lens 13 are provided at the tip part 8. An end surface (an end surface of the emanating side) of a light guide fiber 14 for transmitting an illuminating light is arranged so as to face the luminous intensity distributing lens 12. The light guide fiber 14 is inserted into the insertion part 2, the operating part 3 and an universal cord 4 and the other end surface of the light guide fiber 14, that is, an end surface of an incident side leads to the light source connector 5 which can be removably connected to a connector receiver of the light source apparatus 20. Then, an illuminating light supplied to this end surface of an incident end side is transmitted so as to emanate the transmitted illuminating light to a subject side and illuminate this subject.

A photoelectric conversion surface of an interline type CCD as a solid state imaging device is provided at the image forming position of the objective lens 13. A micro lens array 59 which increases the quantity of light entering each pixel as mentioned below is arranged in front of the photoelectric conversion surface of the interline type CCD 15.

A signal line 18, which is connected to the CCD 15, for transferring driving signals and output signals is inserted into the insertion part 2, the operating part 3, the universal cord 4, the light source connector 5 and the electric cable 8, and connected to the electric connector 7. Also, a channel for treating tools 18 in which treating tools can be inserted is provided in the insertion part 2 and the operating part 3. The tip of the channel 18 is opened at the tip part 8 and the rear end is connected to an insertion entrance 19 provided on the operating part 3 as shown in FIG. 12.

The light source apparatus 20 comprises a lamp 21, a power supply 22 supplying power to the lamp 21, a lens 23 converging lights emanated from the lamp 21 and making the lights enter the incident end of the light guide fiber 14, a rotating filter 24 provided between the lens 23 and the incident end of the light guide filter 14, and a motor 25 for rotating the rotating filter 24. A red filter 24R, a green filter 24G and a blue filter 24B transmit the lights of a wavelength range of red(R), green (G) and blue(B), respectively, are arranged along the direction of the circumference of this rotating filter 24. By rotating the rotating filter 24 by the motor 25, the light from the lamp 21 is colored with red, green and blue lights passing through the red, green and blue filters 24R, 24G and 24B, in order. These red, green and blue lights are applied to the incident end of the light guide fiber 14 and sequentially illuminate the subject through the luminous intensity distributing lens 12. Thus, this embodiment uses a frame sequential system which sequentially switches the illuminating light to red, green and blue lights.

The video processor 30 comprises a driving circuit 31 connected to the CCD 15 through the signal line 16 and a video signal processing circuit 32. Then, a photoelectrically converted signal charge is read and becomes a video signal by applying the driving signal (see FIG. 14b, c, d) to the CCD 15 from the driving circuit 31. The video signal is processed in the video signal processing circuit 32 so that a standard video signal is produced. Then, the video signal from the video signal processing circuit 32 is supplied to the CRT monitor 35 so that a subject image is displayed on the CRT monitor 35.

A treatment tool, such as a laser probe 40 is inserted into the channel for treatment tools 18. A connector 41 is provided at the base of the laser probe 40 and connected to a laser apparatus 42. Also, a foot switch 43 for operating the laser apparatus 42 is connected to the laser apparatus 42. Further, the laser apparatus 42 is provided with a laser which sends out a laser beam for treatment and a laser which sends out a guiding light. The light emitted from each laser passes through the laser probe 40 and emanates from the tip part of the laser probe 40 so that the beam can apply to an affected part 44 as shown in FIG. 12. The treatment including excision or burning is given by the laser beam for treatment so that the applied part of the laser beam can be identified by the guiding light.

Figure 13A:
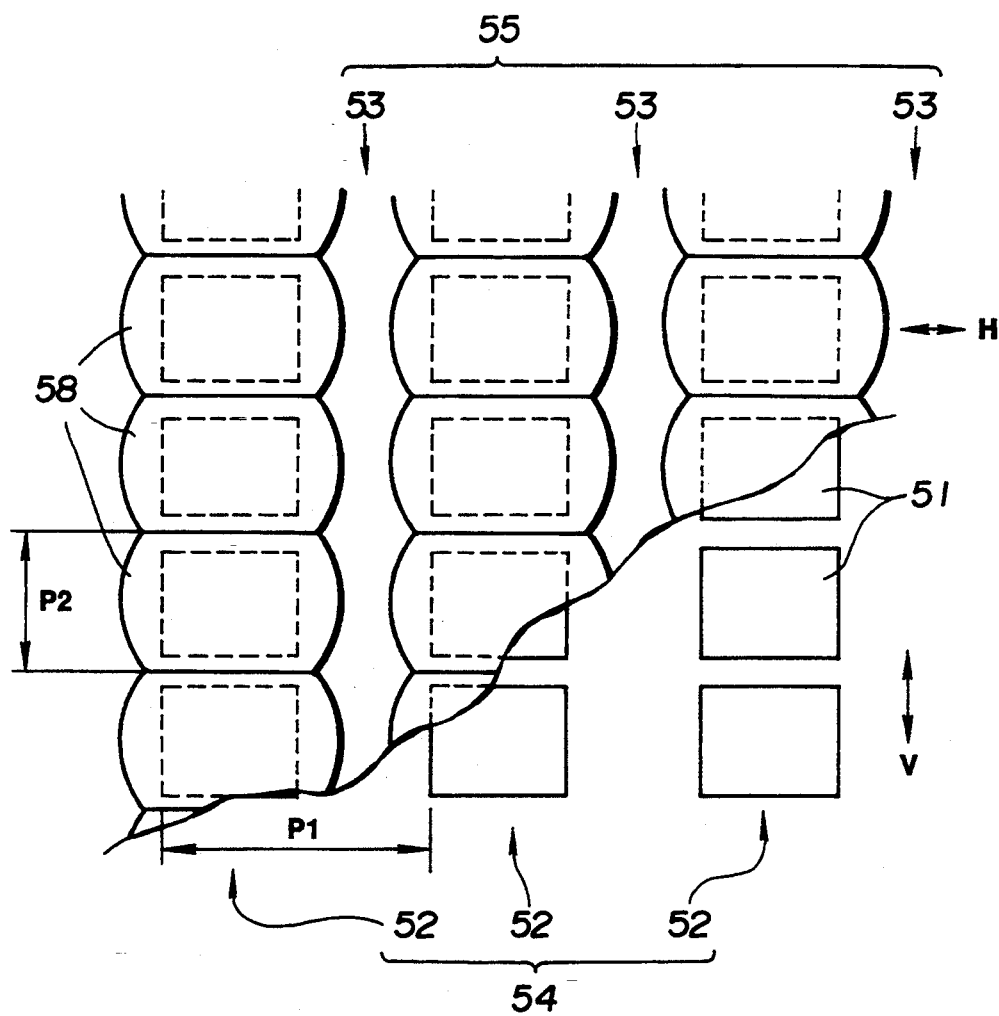
FIGS. 13a, b, and c are illustrations showing main parts of a CCD.

As shown in FIG. 13a, in the interline type CCD 15, a photodiode array 52 is formed by arranging photodiodes 51, which photoelectrically convert, at a regular pitch P2, in the vertical direction V and a vertical transfer path 53, which transfers a charge, are alternately arranged as adjoining each other in the horizontal direction (traverse direction) H in parallel with the photodiode arrays 52, and a sensitive part (sensor part) 54 consists of the photodiode arrays 52, 52 . . . , and a vertical transferring part (V. CCD, hereinafter) 55 for vertically transferring a photoelectrically converted charge (signal) in the sensitive part 54 consists of vertical transfer paths 53, 53 . . . , which stretches in the vertical direction V.

Figure 14A:
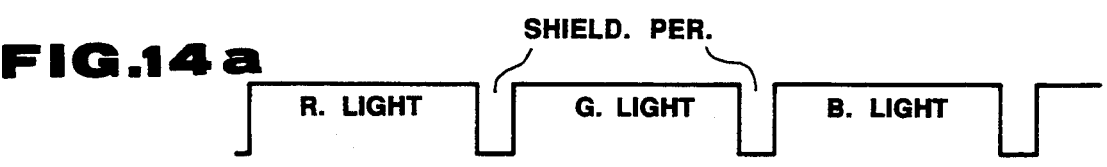
FIG. 14 is a timing chart showing a driving signal applied to a CCD.
Figure 14B:
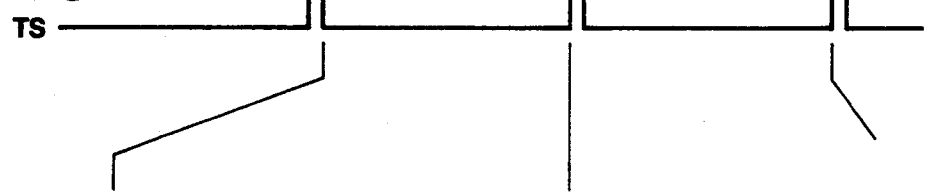
Figure 14C:
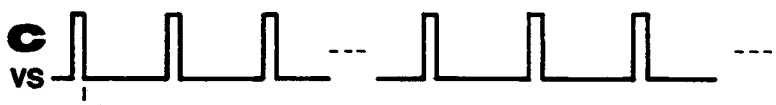
Figure 14D:

Each photodiode array 52 consists of the photodiodes 51, 51 . . . , and each vertical transfer path 53 is applied by a transfer signal TS (shown in FIG. 14b) supplied from the driving circuit 31 when the illuminating light is broken as shown in FIG. 14a so that the charges of the photodiodes 51, 51 . . . , adjacent to the photodiode array 52 is transferred to a vertical transfer pixel part and further transferred in the vertical direction by applying a vertical transfer signal VS (FIG. 14c). The charge of the final pixel part of the vertical transfer paths 53, 53 . . . , is transferred to a horizontal transfer resistor (see FIG. 16) which is adjacently provided to the path 53. The charge transferred to the horizontal transfer resistor is successively output as a video signal from the output end of the horizontal transfer resistor by applying a horizontal transfer signal HS shown in FIG. 14d. In FIG. 14a, a short shielding light period formed after each frame sequential illuminating period (e.g. shown as R. LIGHT) is provided to prevent colors of the illuminating light from mixing and corresponds to the shielding light part formed between filters which are adjacent to each other (e.g., the filters 24R and 24G) by only the length of a diameter of an irradiating beam to the rotating filter 24.

On the photoelectric conversion surface of this CCD 15, unit pixel (the pitch is represented by P1) is composed of one photodiode 51 and the vertical transfer pixel part being adjacent to the photodiode 51 in the horizontal direction and unit pixel is composed of one photodiode 51 by a pitch of P2 in the vertical direction. Also, a shielding light aluminum 57 is provided on the surface of the V. CCD 55. Even if light enters the photoelectric conversion surface, a charge can be transferred without having an effect of the light.

Figure 13B:
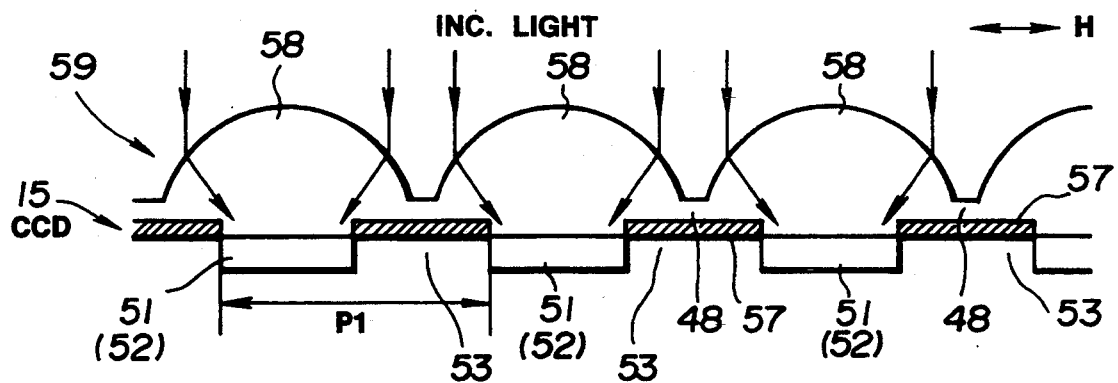
Figure 13C:
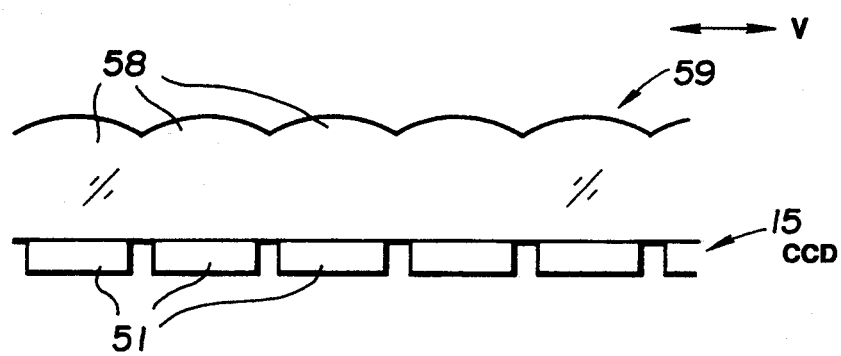

In this embodiment, as shown in FIGS. 13b and 13c, a micro lens array 59 which is a minute optical lens is fitted to every unit pixel just in front of the photoelectric conversion surface in the manner in which a convex micro lens 58 is arranged in every unit pixel.

This micro lens array 59 is connected to the micro lens 58 as an unit by a connecting member 48 so that each lens 58 is placed opposite to the center of the pixel of each photodiode 51. As shown in FIG. 13b, the size (area) of the convex part of each micro lens 58 is made larger than the pixel size of the photodiode 51.

Therefore, as shown by the arrows in FIG. 13b, when an incident light enters the vertical transfer pixels (vertical transfer paths 53,53) parts on both sides of the pixel of the photodiode 51, the light is refracted in the direction of the optical axis by the micro lens 58 and is to enter the photodiode 51 arranged opposite to the lens 58 on the optical axis.

That is to say, because the micro lens 58 is not provided in prior art, a light is not received by the photodiode 51 and enters the vertical transfer paths 53, 53 which surrounds the photodiode 51 so that part of the incident light is thrown away when the incident light enters both sides of the photodiode 51. On the other hand, in this embodiment, part of the light entering the vertical transfer paths 53, 53 around the photodiode 51 is converged on the side of the photodiode 51 so as to increase the quantity of light received by the photodiode 51. In other words, the photodiode 51 has the same function as the photodiode having a larger pixel size. Also, as shown in FIG. 13c, the size (length) of the micro lens 58 is larger than the actual pixel size of the photodiode 51 in the vertical direction so that the photodiode 51 has a function for increasing the quantity of the incident light in this direction. In this diagram, although the function for increasing the quantity of light does not become larger because the pixels of the photodiodes 51, 51 . . . , are very closely arranged, the function become larger in more sparsely arranged pixels.(therefore, it is effective to equip the micro lens array with the CCD, such as a line transfer type CCD or a frame transfer type CCD which is different from the interline type CCD 15 having the transfer path 53 being adjacent to each photodiode 51.)

In this embodiment, because a micro lens array 59 is provided on the photoelectric conversion surface so as to make each micro lens 58 arranged opposite to each pixel of the sensitive part 54, the effective aperture ratio of the sensitive part 54 of the CCD 15 increases and its sensitivity becomes higher. Also, the effective aperture ratio of the sensitive part 54 can be increased so that a small solid state imaging device having smaller pixels can be used.

Also, since the interline type CCD 15 having a transfer part 55 which can transfer charges without having an effect of an incident light is used as a solid state imaging device, the generation of smear and blooming can be prevented even when the laser beam and guiding light from the laser probe 40 is applied to the subject. In this embodiment, in order to prevent the smear or blooming caused by the laser beam, the interline type CCD 15 is used and also, the micro lens array 89 for increasing the quantity of the light incident on the sensitive part 54 is provided so that the low sensitivity is compensated only in the interline type CCD.

By the electronic endoscope 1 in this embodiment, even in an electronic endoscope of very small size for thin tube cavity, such as bronchi or blood vessels, the sensitivity can be improved and also medical treatment with a laser beam (such as laser angioplasty) can be applied under a high quality picture image.

Next, the second embodiment of this invention is explained with reference to FIGS. 15 to 17.

This embodiment is an example of an electronic endoscope apparatus fitting a TV camera outside 60 in which a TV camera 63 fitting outside is attached to an eyepiece part 62 of a fiberscope 61.

Figure 15:
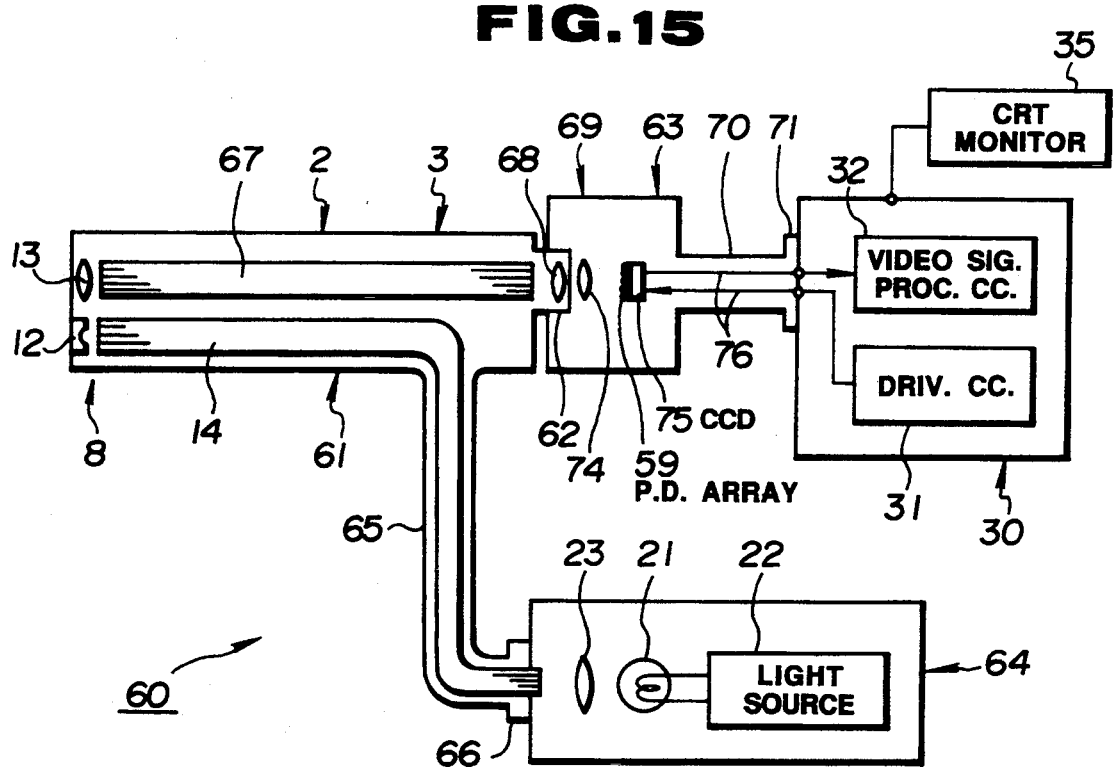
FIGS. 15 to 17 relate to the second embodiment of this invention and FIG. 15 is an illustration showing the whole structure of an electronic endoscope apparatus of the second embodiment.

As shown in FIG. 15, the electronic endoscope apparatus 60 comprises a fiberscope 61, a light source apparatus 64 to which this fiberscope 61 is connected, the TV camera fitted outside which is connected to the eyepiece part 62 of the fiberscope 61, a video processor 30 to which the TV camera 63 is connected and a CRT monitor 35 which is connected to this video processor 30.

The fiberscope 61 comprises an elongated flexible insertion part 2, an operating part 3 fitted to the rear end of this insertion part 2, the eyepiece part 62 provided at the rear end of this operating part 3, a light guide cable 65 extended from the operating part 3 and a connector 66 provided at the end part of this light guide cable 65 and removably connected to the light source apparatus 64. A luminous intensity distributing lens and an objective lens 13 are provided at the tip part of the insertion part 2.

An end surface of the emanating side of the light guide fiber 14 is arranged at the rear end of the luminous intensity distributing lens 12. This light guide fiber 14 is inserted into the insertion part 2, the operating part 3 and the light guide cable 65 and the end surface of the incident side leads to the connector 66. Also, a tip surface of an image guide fiber 67 for transmitting an optical image is placed in an image forming position of the objective lens 13. This image guide fiber 67 is inserted into the insertion part 2 and the operating part 3 and the rear end surface of the image guide fiber 67 is opposed to an eyepiece lens 68 within the eyepiece part 62.

The light source apparatus 64 comprises a lamp 21, a power source 22 supplying power to this lamp 2 and a lens 23 which converges a light emitted from the lamp 21 and make the light enter the incident end of the light guide fiber 14.

The TV camera 63 comprises a camera head 69 removably connected to the eyepiece part 62, a cable 70 extended from the camera head 69 and a connector 71 provided at the end of the cable 70 and removably connected to the video processor 30.

The camera head 69 is provided with an image forming optical system 74 forming an image observed from the eyepiece part 62 and a CCD 75 placed on the image forming position of this image forming optical system 74. A cable line 76 for transferring driving signals and output signals connected to the CCD 75 is inserted in the cable 70 and connected to the connector 71.

The video processor 30 comprises a driving circuit 31 connected to the CCD 75 through the signal line 76 and a video signal processing circuit 32. The CCD 75 is driven by the driving circuit 31 and the output signal of the CCD 75 is processed in the video signal processing circuit 32. The video signal from the video signal processing circuit 32 is supplied to the CRT monitor 35 so that a subject image is displayed on the CRT monitor 35. Also, in this embodiment, the video processor 30 corresponds to a simultaneous type.

Figure 16:
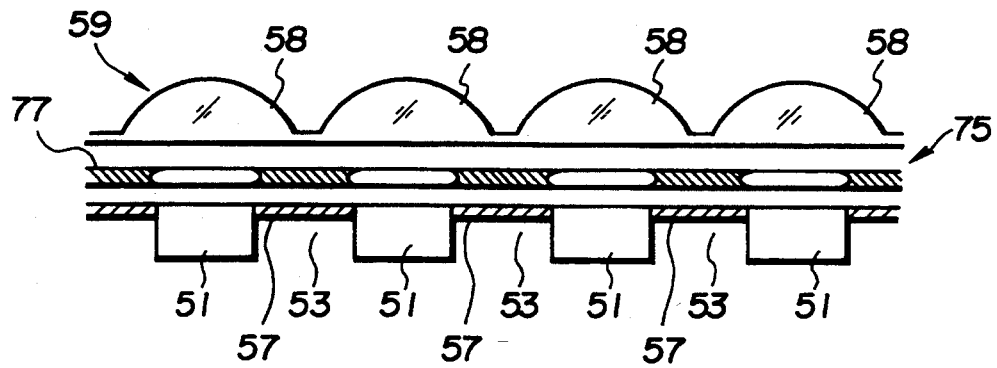
Figure 17:
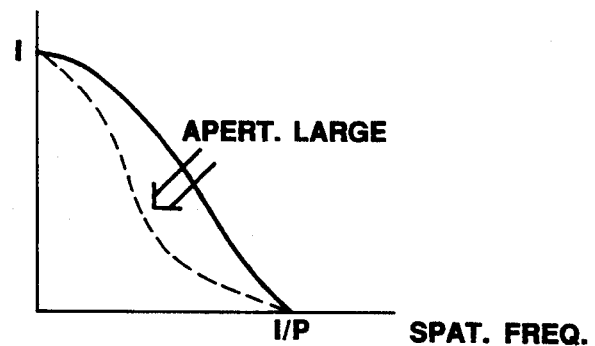

As shown in FIG. 16, the CCD 75 is an interline type CCD and a sensor part 51 composed of photodiodes is adjacently placed to and a V.CCD 52. A shielding light aluminum 57 is provided on the surface of the V.CCD 52. Since a simultaneous type is used as a color imaging system in this embodiment, a color filter 77 for separating colors is provided on the surface of the CCD 75. Also, like the first embodiment, a micro lens array 59 is provided just in front of the photoelectric conversion surface of the CCD 75 so that a convex micro lens 58, which is a minute optical lens, is arranged in every unit pixel of the CCD 75.

The other structure is the same manner as the first embodiment. In this embodiment, a white illuminating light emitted from the light source 64 is transmitted by the light guide fiber 14 and irradiated on the subject through the end surface on the side of the tip part 8 and the luminous intensity distributing lens 12. The subject image is formed on the tip surface of the image guide fiber 65 by the objective lens 13 and transferred to the end surface of the side of the eyepiece part 62 by this image guide fiber 65. Futher, this subject image is formed on the CCD 75 by the image forming optical system 74 of the outside fitting TV camera 63, and photoelectrically converted by the CCD 75.

Since the CCD 75 is provided with a micro lens 58 in every unit pixel, the aperture ratio increases. As shown in FIG. 17, the MTF changes in the direction from the solid line to the broken line with the increase of the aperture ratio. In this case, the spatial frequency of threshold resolution scarcely changes and the modulation characteristic falls in the side of the high stage. Accordingly, the increase of the aperture ratio can reduce the moire cause by a pitch of the image guide fiber 67 and a spatial sampling of the CCD 75 without lowering the threshold resolution. Thus, a crystal optical filter(low pass filter) required for reducing the moire in the prior art is not needed and the TV camera 63 can be highly sensitive and small. Also, FIG. 17 shows the MTF provided that the pitch of an unit pixel of the CCD 75 sampling is P.

The other operations and effects are the same as the first embodiment.

Figure 18:
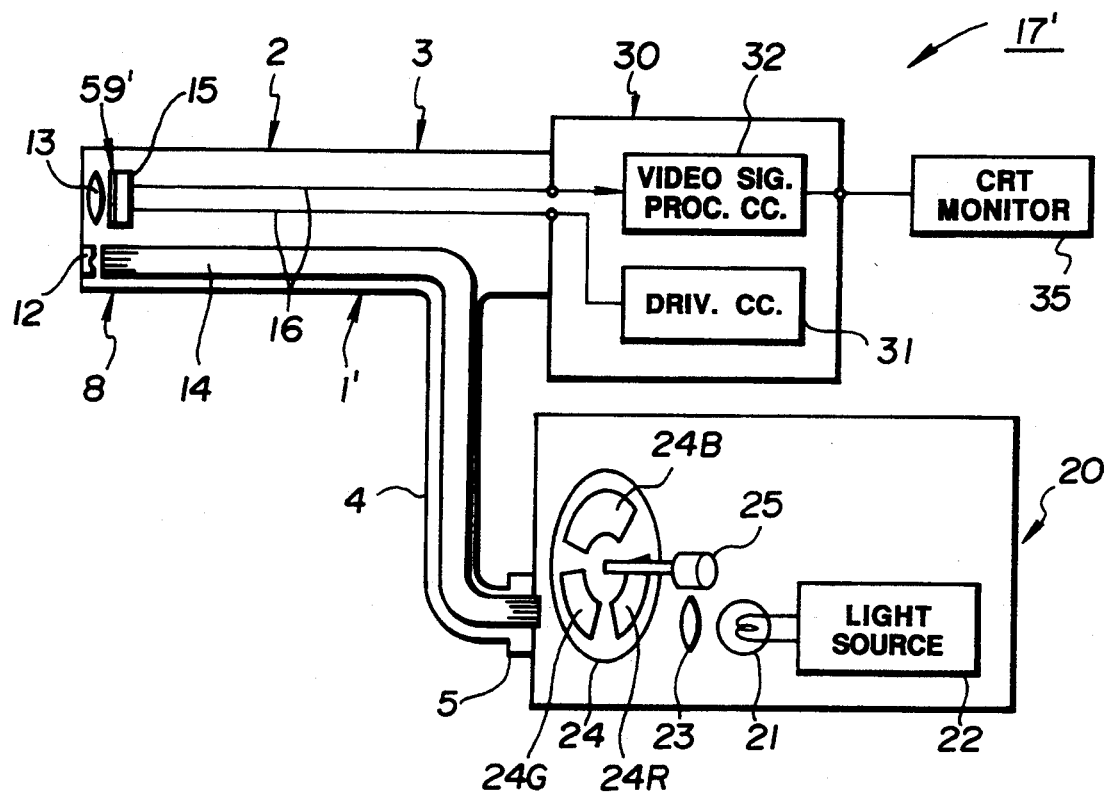
FIGS. 18 and 19 relate to the third embodiment of this invention and FIG. 18 is an illustration showing the whole structure of an electronic endoscope apparatus of the third embodiment.
Figure 19:
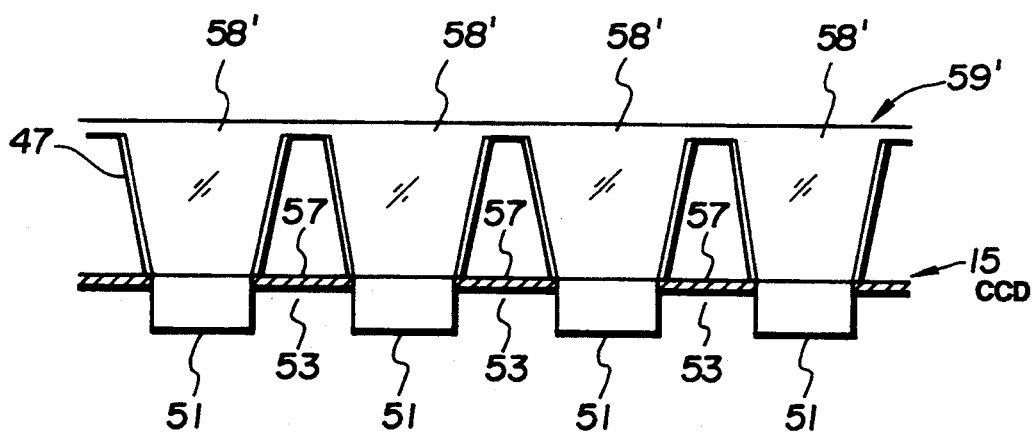

Next, the third embodiment of this invention is explained with reference to FIGS. 18 and 19. In an electronic endoscope apparatus 17' of the third embodiment, an electronic endoscope 1' is used. In the endoscope 1', a conical reflecting lens array 59' in which conical reflecting lenses 58' (see FIG. 19) instead of the micro lenses 58 in the first embodiment shown in FIG. 11 are arranged and fitted to the interline type CCD 15. Also, a laser apparatus 42 is not used in this embodiment.

In the interline type CCD 15, a photodiodes 51 (consists of the sensitive part) and a vertical transfer paths 53 (consists of the vertical transfer part) are alternately arranged in the horizontal direction. A unit pixel (one pixel) is composed of one photodiode 51 and a pixel part of one vertical transfer path which is adjacent to the photodiode 51 in the horizontal direction. Also, a shielding light aluminum 57 is provided on the surface of the vertical transfer path 53.

In this embodiment, the conical reflecting lens 58' is fitted on the photoelectric conversion surface of the CCD 15 by every pixel. This conical reflecting lens 58' is made of plastic, for example, and the light passing through the lens 58' is reflected by the side of the lens 58'. Also, the shape of the conical reflecting lens 58' is conical or pyramidal and the sectional area of the lens 58' becomes larger with increasing the distance from the side of the photodiode 51 to the side of the objective lens 13. For example, the size of the end surface faces the photodiode 51 is formed as the same size as the pixel size of the photodiode 51. (Accordingly, the size of the end surface of the objective lens 13 becomes larger).

Therefore, even if a light incident light on the photoelectric conversion surface of the CCD 15 through the objective lens 13 enters the surroundings of the pixel of the photodiode 51, the light is reflected by the side of the conical reflecting lens 58' and converged on the side of the photodiode 51. Also, a reflecting film 47 for making the reflection of the light easy can be provided on the side of the conical reflecting lens 58'. The other structure is the same manner as shown in the first embodiment and the same mark is given to the same constructing member, thus, the explanation of the member is omitted.

In the electronic endoscope apparatus 17' comprising the CCD 15 constructed as mentioned above, because a conical reflecting lens array 59' is provided on the surface of the photoelectric conversion surface so that the conical reflecting lens 58' is faced by every pixel, a light enters on the surroundings of the sensitive part of the photoelectric conversion surface (of the photodiode 51) in which the reflecting lens 58' is not provided and does not contribute toward imaging is reflected by the side of each conical reflecting lens 58' and converged on each photodiode 51. Therefore, as shown in the first embodiment, the effective aperture ratio of the CCD 15 can be increased and the sensitivity can be improved.

As shown in this embodiment, like the first embodiment, the sensitivity can be improved and a high quality picture image can be obtained where the solid state imaging device becomes smaller.

Figure 20:
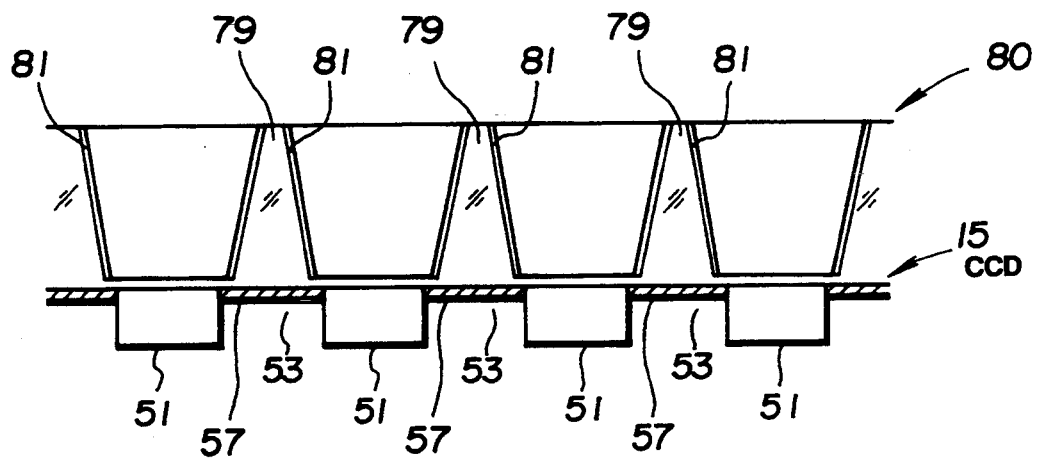
FIG. 20 is an illustration showing the structure of a main part of a CCD of the fourth embodiment of this invention.

FIG. 20 shows the structure of the main part of a CCD in the fourth embodiment of this invention.

As shown in this diagram, the fourth embodiment uses a reflecting lens array 80 in which many concave reflecting lens parts 79 are formed in a body as an optical device attached to the photoelectric conversion surface of the CCD 15. That is to say, the part of each conical reflecting lens 58' in FIG. 19 is made an aperture part and a reflecting part is provided around the aperture part to form each reflecting lens part 79.

A reflecting film 81 is evaporated on each concave reflecting lens 79 so that the inner surface of the aperture part reflects the light. Also, the aperture part is shaped like the one in which the aperture size on the side of the photodiode 51 gradually becomes smaller like the reflected light converged on the side of the photodiode 51. The other parts are formed as shown in the same manner as the third embodiment.

Also, if such a concave reflecting lens 79 is attached on the photoelectric conversion surface of the CCD 15, a light enters the surrounding part of the photodiode 51 which forms the sensitive part where the reflecting lens 79 is not provided as shown in the third embodiment, and the light, which is not received by the photodiode 51, is reflected by the side of the aperture part of the concave reflecting lens 79 and converged on the photodiode 51. Thus, the effective aperture ratio of the CCD 15 increases and the sensitivity becomes higher.

Therefore, also in the fourth embodiment, the sensitivity can be improved where the solid state imaging device becomes smaller, so that a high quality picture image can be obtained.

Figure 21:
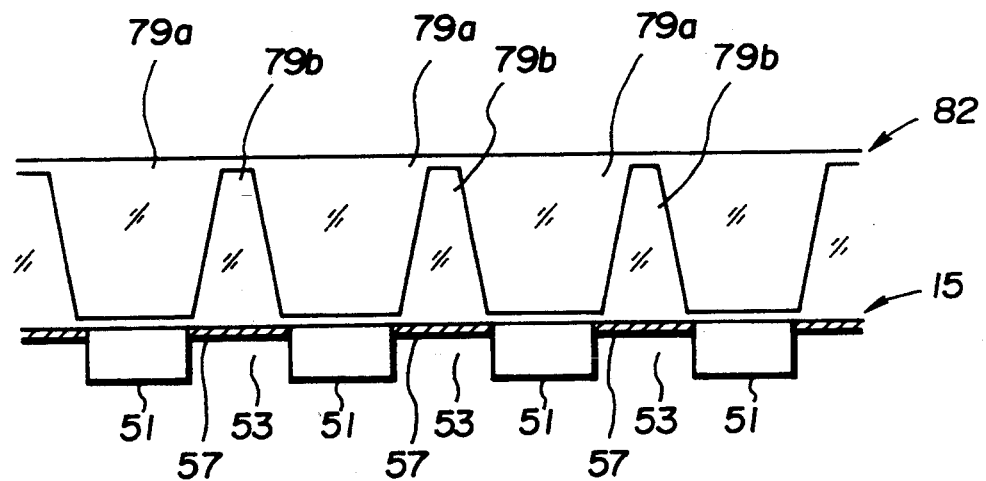
FIG. 21 is an illustration showing the structure of a main part of a CCD of the fifth embodiment of this invention.

FIG. 21 is an illustration showing the main part of the CCD in the fifth embodiment of this invention.

As shown in FIG. 21, a complex reflecting lens array 82 made of a refractive index complex type reflecting lenses 79a and 79b as an optical device attaching to the photoelectric conversion surface of the CCD 15 is used in the fifth embodiment. The complex reflecting lens array 82 is composed of complex lens arrays in which the convex part of the lens 79a having a high refractive index and concave part of the lens 79b having low refractive index are joined are arranged in the position faced by the front surface of the photodiode 51. The boundary between the high refractive index lens 79a and low refractive index lens 79b reflects a light. The reflecting film 47 is not provided. The other parts are similarly formed like the third embodiment.

Also, where such refractive index complex type reflecting lenses 79a and 79b are attached to the photoelectric conversion surface of the CCD 15, a light enters the surrounding part of the photodiode 51 if the reflecting lens is not provided and the light which does not enter the photodiode 51 is reflected by the boundary of the lenses 79a of a high refractive index and 79b of a low refractive index and converged on the photodiode 51 in the same way as the third embodiment. Thus, the effective aperture ratio of the CCD 15 increases and the sensitivity becomes higher.

Therefore, also in the fifth embodiment, the sensitivity can be improved where the solid state imaging device become smaller so that a high quality picture image can be obtained.

Also, as a modification of the fifth embodiment of the fifth embodiment, a filter can be arranged between the above mentioned optical device and the photoelectric conversion surface.

Figure 22:
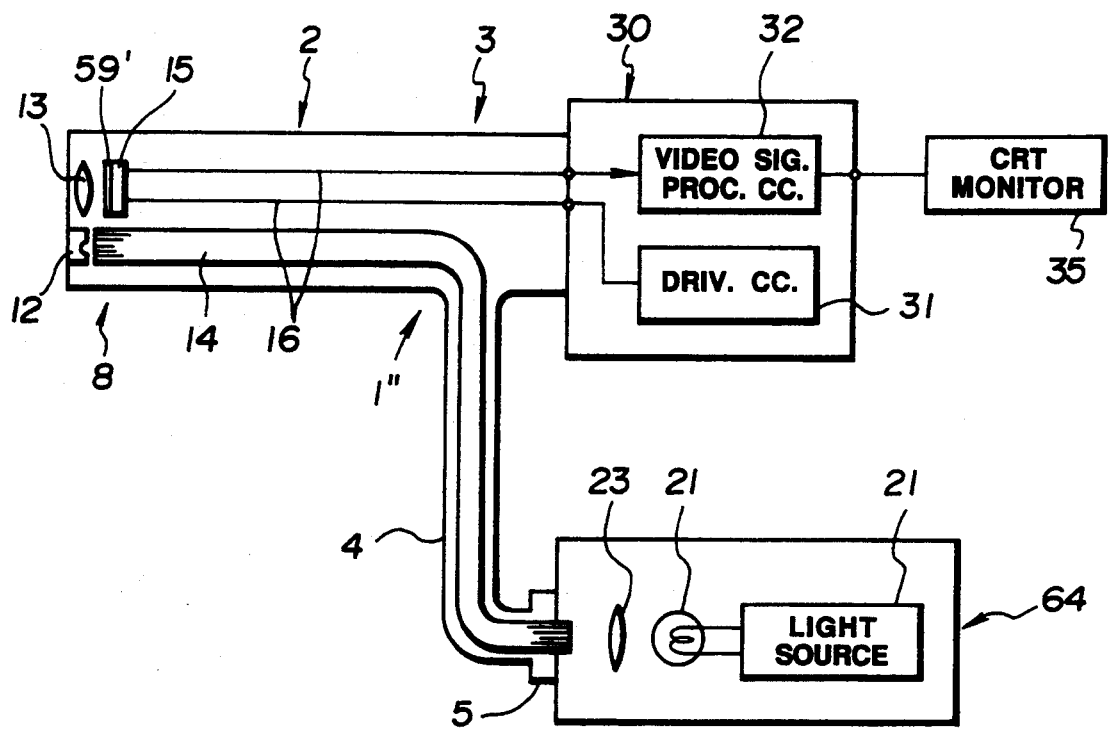
FIGS. 22 and 23 relate to a modification of the fifth embodiment and FIG. 22 is an illustration showing the whole structure of an electronic endoscope apparatus of this modification.

As shown in FIG. 22, an electronic endoscope apparatus of this modification comprises an electronic endoscope 1, a light source apparatus 64 to which this electronic endoscope 1 is connected, a video processor 30 and a CRT monitor 35 connected to the video processor 30.

In this modification, a simultaneous system is used as a color imaging system. The light source apparatus 64 comprises a lamp 21, a power supply 22 supplying power to this lamp 21 and a lens 23 converging lights emitted from the lamp 21 and make the lights enter the incident end of the light guide fiber 14. Also, the video processor 30 corresponds to the simultaneous system. The other elements of the structure of the endoscope apparatus is similarly formed as the third embodiment.

Figure 23D:
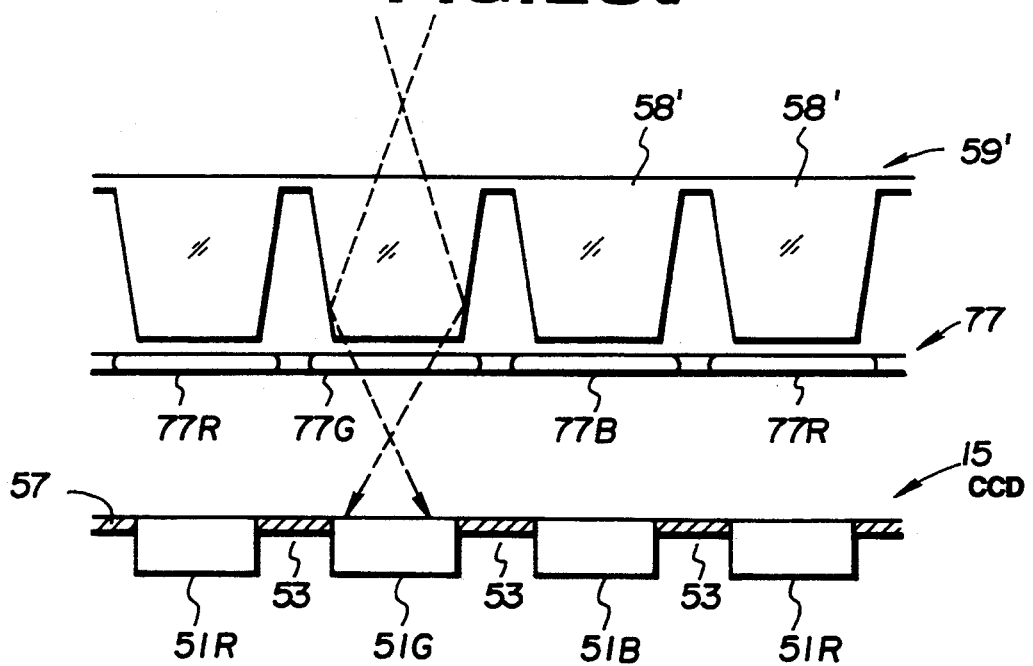
FIGS. 23a and 23b are illustrations showing a CCD of this modification and a main part of a CCD which is not provided with a conical reflecting lens to compare with the CCD of the modification.

As shown in FIG. 23a, a CCD 15 is an interline type CCD, and a photodiode 51 (photodiode array 52) forming a sensitive part and V. CCD 53 are adjacently and alternately arranged. A shielding light aluminum 57 is provided on the surface of the V. CCD 53. In this modification, since a simultaneous system is used as a color imaging system, a color filter for separating colors 77 is provided on the surface of the CCD 15. In the same manner as the third embodiment, a conical reflecting lens 58' as an optical device is arranged opposite to every unit pixel of the photoelectric conversion surface of the CCD 15.

In this modification, a white illuminating light emitted from the light source apparatus 64 is irradiated on a subject through the light guide fiber 14 and a luminous distributing lens 12. The subject image is formed on the CCD 15 by an objective lens 13 and photoelectrically converted by the CCD 15.

Figure 23B:
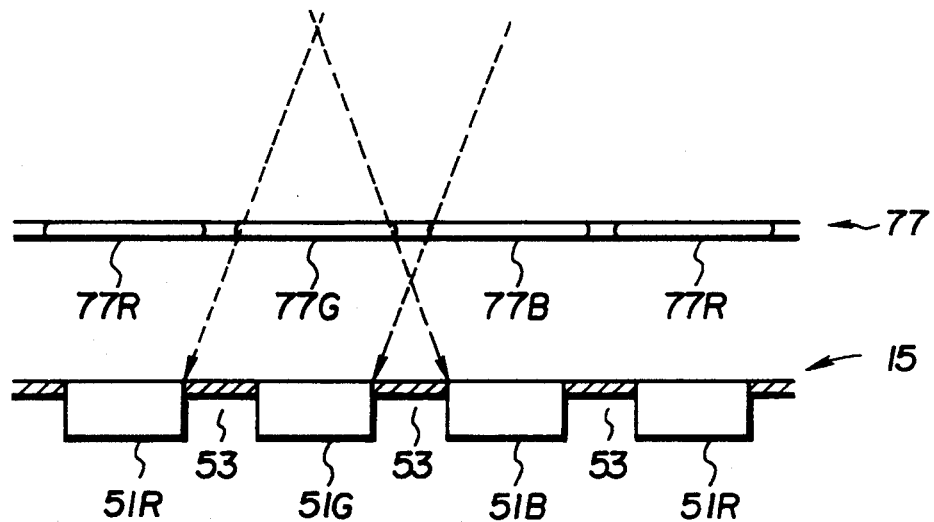

When light colors of red, green and blue are separated in every pixel by using the color filter 77, as the prior art shown in FIG. 23b, for example, a light passed through a color filter 77B for blue color sometimes enters a photodiode 51G for green color which is adjacent to the color filter 77B. Therefore, there is a problem in which the colors are mixed in the photodiode 51G and color reproducibility becomes worse. Especially in the endoscope, in order to make a visual field a wide angle, a lens such as a fish-eye lens is used for the objective lens 13, therefore, problems are liable to occur in which a light obliquely enters and colors are mixed as the mentioned above.

In the meantime, by fitting the conical reflecting lens 58' in front of the color filter 77 as shown in this modification, the obliquely incident light is reflected by the side of the reflecting lens 58' as shown in FIG. 23a and converged by the photodiode 51G through the color filter 77G for green color, for example.

Thus, on the CCD provided with the color filter, an obliquely incident light is reflected by the boundary surface of the optical device so that the light does not enter the adjacent photodiode. Accordingly, the colors in the sensor part are prevented from mixing and the color reproducibility can be improved. Also, because the incident light is converged on each sensor part, the sensitivity can be improved under the condition of smaller solid state imaging device like the third embodiment so that a high quality picture image can be obtained.

Also, in this modification, the optical device attached on the color filter 77 is not limited to the conical reflecting lens 58' and lenses including the concave reflecting lens 79 of the fourth embodiment and the refractive index complex type reflecting lenses 79a and 79b of the fifth embodiment can be also used.

Figure 24A:
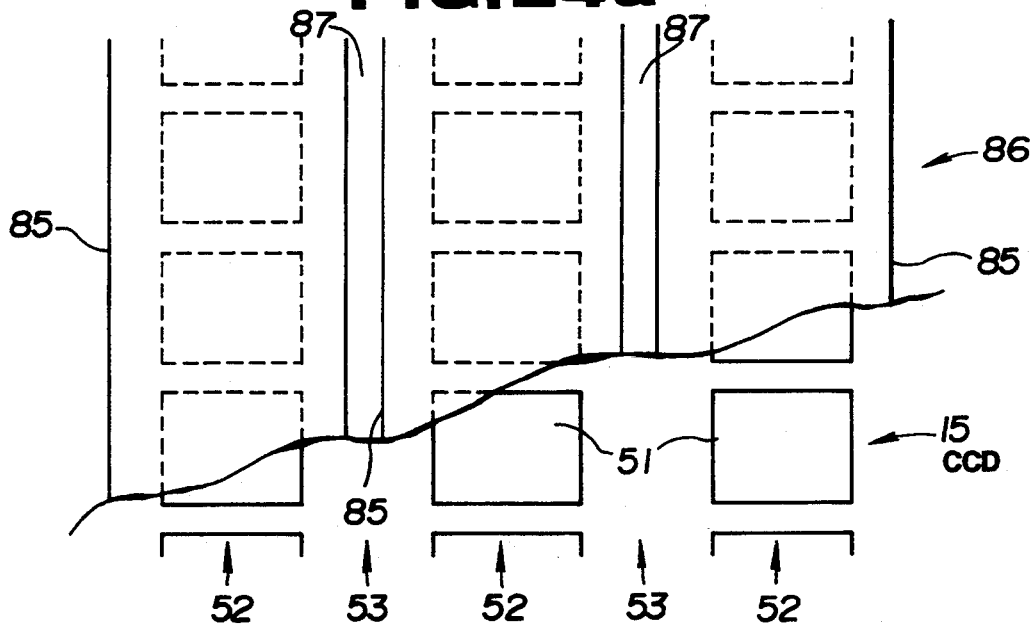
FIG. 24a is a plan view showing a CCD of the sixth embodiment of this invention.

In each embodiment mentioned above, a converging light device, such as a micro lens 58 is arranged opposite to each pixel forming the sensitive part; however, each converging device can be arranged by each of a plurality of pixels of the sensor part as explained by referring to FIG. 24 (one line of the number of pixels of the sensitive part in this embodiment).

In this embodiment, instead of the micro lens array 59 in the first embodiment shown in FIG. 13, for example, a cylindrical lens array 86 is attached so that a cylindrical lens 85 linearly extending in the vertical direction is placed opposite to each photodiode array 52 linearly arranged in the vertical direction. That is to say, a cylindrical lens 85 (as an optical device) is arrange to face a plurality of the photodiodes 51, 51 . . . , linearly arranged in the vertical direction.

Figure 24B:
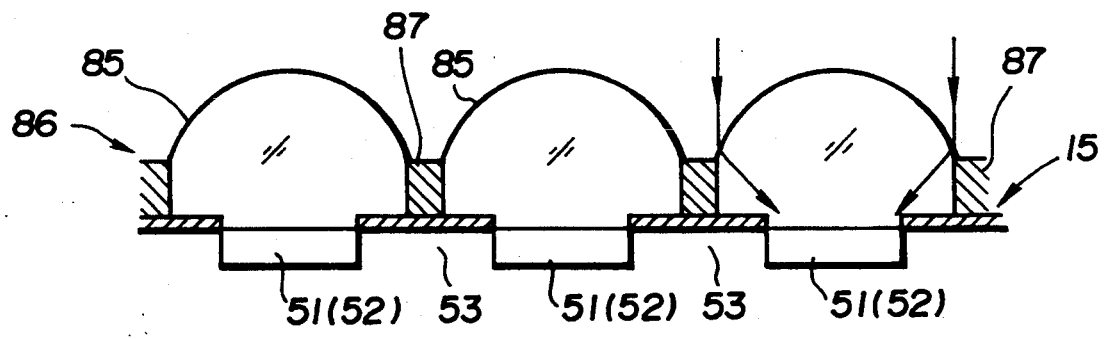

Each cylindrical lens 85 is a convex lens having a function of converging lights in the horizontal direction meeting at right angles with the lengthwise direction as shown in FIG. 24b. In the meantime, the lens 85 does not have a function of converging light in the vertical direction. Therefore, as explained in the first embodiment, each cylindrical lens 85 has a function of refracting a light incident on the both sides of the photodiodes 51, 51 . . . , to the inside, converging it and making the photodiodes 51, 51 . . . , receive the light. As shown in FIG. 24b, the cylindrical lenses 85, 85 adjoining each other are connected with a shielding light member 86 (so that the light does not leak out to the neighborhood) and the shielding light member can be made of the same material of glass or plastic as the cylindrical lens 85.

According to this embodiment, the structure of the cylindrical lens array 86 as a converging light device array is simplified so that a converging light device array can be relatively easily formed.

In this embodiment, although one cylindrical lens 85 is arranged opposite to a vertical line of the photodiode 51, 51 . . . , a plurality of the cylindrical lenses can be arranged opposite to a line of the photodiodes 51, 51 . . .

Also, this invention can be applied not only to the interline type CCD, but also to the frame transfer type CCD which has a sensitive part on which a plurality of photoelectric conversion pixels for photoelectrically converging are two-dimensionally arranged and a transfer part, being adjacent to the sensitive part, for transferring a signal transferred from the sensitive part to the vertical or horizontal direction and also to the line transfer type CCD which has a sensitive part on which a plurality of photoelectric conversion pixels for photoelectrically converging are two-dimensionally arranged and the sensitive part has a function of the transfer part for transferring a photoelectrically converted signal. That is effective in improving the sensitivity and obtaining a high quality picture image.

Also, this invention can be applied to a solid state imaging device other than a CCD.

Further, the endoscope of each embodiment mentioned above (for example, FIG. 11) uses the light guide 14 whose end surface of the tip side emits a transmitted illuminating light; however, by housing a lamp for emitting a white light on the side of the emitting end surface or a plurality of LED or the like, a white illuminating light or a frame sequential light can emanate from this lamp or LED to the side of the subject.

Further, parts of above mentioned embodiments can be combined to compose different embodiments and these embodiments are included in this invention.

What is claimed is:

1. An electronic endoscope apparatus comprising:
   an electronic endoscope having an elongated insertion part, an illuminating light emitting means for emitting an illuminating light from a top side of the insertion part, an objective optical system provided at the tip side of said insertion part for forming an optical image of a subject illuminated by said illuminating light, an interline type charge coupled device objective optical system, and a converging light device array provided with at least one converging light device having an MTF characteristic of increasing a quantity of incident light entering at least one photoelectric conversion pixel and lowering a value of a modulation characteristic around a pitch of said photoelectric conversion pixel so as to reduce moire, said at least one photoelectric conversion pixel provided in front of a photoelectric conversion surface of said interline type charge coupled device, each of said at least one converging light device arranged on a respective one of said at least one photoelectric conversion pixel;
   a driving signal generating means for supplying a driving signal to said interline type charge coupled device;
   a video signal processing means for processing a standard video signal supplied from said interline type charge coupled device by applying said driving signal and generating a standard video signal; and
   a monitor means for displaying said standard video signal;
   wherein said electronic endoscope is a TV camera fitting outside endoscope comprising an optical endoscope arranged by an end surface of an image guide formed of fiber bundles in the image forming position of said objective optical system, and transmitting the optical image to another end surface of the image guide, and a TV camera fitted opposite to the another end surface and having said interline type charge coupled device inside.

2. The electronic endoscope apparatus of claim 1 wherein said illuminating light emitting means is a white light emitting means for emitting a white light.

3. The electronic endoscope apparatus of claim 1 wherein said illuminating light emitting means is a frame sequential light emitting means for sequentially emitting lights of different wavelength ranges.

4. The electronic endoscope apparatus of claim 1 wherein a color filter for optically separating colors is arranged in front of the photoelectric conversion surface of said interline type charge coupled device.

5. The electronic endoscope apparatus of claim 4 wherein said color filter is arranged between the photoelectric conversion surface of said interline type charge coupled device and said converging light device array.

6. The electronic endoscope apparatus of claim 1 wherein each of said at least one converging light device is arranged opposite to a respective one of said at least one photoelectric conversion pixel.

7. The electronic endoscope apparatus of claim 1 wherein said interline type charge coupled device is alternately composed of a photoelectric conversion pixel array arranged by a plurality of photoelectric conversion pixels along a line, and a transfer path for transferring a transferred signal from the photoelectric conversion pixel array, the transfer path being adjacent to the photoelectric conversion pixel array and in parallel with the photoelectric conversion pixel array.

8. The electronic endoscope of claim 7 wherein said converging light device array is a cylindrical lens array arranged opposite to one or more cylindrical lens being convex in a direction meeting at right angles with the line in every said photoelectric conversion pixel array arranged along said line.

9. The electronic endoscope apparatus of claim 1 wherein said converging light device array is a convex lens array provided with a convex lens, as said each converging light device, having a larger area than the area of each of said photoelectric conversion pixel, the convex lens arranged opposite to said each photoelectric conversion pixel.

10. The electronic endoscope apparatus of claim 9 wherein said convex lens array has a shielding member arranged between adjacent convex lenses.

11. The electronic endoscope apparatus of claim 1 wherein said converging light device array is a conical lens array provided with a conical lens, as said each converging light device, having a larger section area than the area of said each photoelectric conversion pixel, the conical lens arranged opposite to said each photoelectric conversion pixel.

12. The electronic endoscope apparatus of claim 1 wherein said converging light device array is a conical reflecting lens array provided with a conical reflecting lens, as said each converging light device, having a larger aperture area than the area of said each photoelectric conversion pixel, the conical reflecting lens arranged opposite to said each photoelectric conversion pixel.

13. An electronic endoscope comprising:
an elongated insertion part;
an illuminating light emitting means for emitting an illuminating light from a tip side of the insertion part;
an objective optical system provided at the tip side of said insertion part, forming an optical image of a subject illuminated by said illuminating light;
an interline type charge coupled device photoelectrically converting the optical image based on said objective optical system; and
a converging light device array provided with converging light devices having an MTF characteristic of increasing a quantity of incident light entering a predetermined number of photoelectric conversion pixels and lowering a value of a modulation characteristic around a pitch of said photoelectric conversion pixel so as to reduce moire, said at least one photoelectric conversion pixel in front of a photoelelectric conversion surface of said interline type charge coupled device, said converging light devices arranged on every at least the predetermined number of the photoelectric conversion pixels;
wherein said electronic endoscope is a TV camera fitting outside endoscope comprising an optical endoscope arranged by an end surface of an image guide formed of fiber bundles in an image forming position of said objective optical system, and transmitting the optical image to another end surface of the image guide, and a TV camera fitted opposite to the another end surface and having said interline type charge coupled device inside.

14. The electronic endoscope of claim 13 wherein a color filter for optically separating colors is arranged in front of the photoelectric conversion surface of said interline type charge coupled device.

15. The electronic endoscope of claim 14 wherein said color filter is arranged between the photoelectric conversion surface of said interline type charge coupled device and said converging light device array.

16. The electronic endoscope of claim 13 wherein said converging light device array is provided with converging light devices increasing the quantity of incident light entering the photoelectric conversion pixel, each of said converging light devices arranged opposite to every said photoelectric conversion pixel.

17. The electronic endoscope of claim 13 wherein said interline type charge coupled device is alternately composed of a photoelectric conversion pixel array arranged by a plurality of photoelectric conversion pixels along a line, and a transfer path for transferring a transferred signal from the photoelectric conversion pixel array, said transfer path being adjacent to the photoelectric conversion pixel array and in parallel with the photoelectric conversion pixel array.

18. The electronic endoscope of claim 17 wherein said converging light device array is a cylindrical lens array arranged opposite to one or more cylindrical lens(es) being convex in a direction meeting at right angles with the line in every said photoelectric conversion pixel array arranged along said line.

19. The electronic endoscope of claim 15 wherein said converging light device array is a convex lens array provided with a convex lens, as said converging light device, having a larger area than the area of each of said photoelectric conversion pixel, said convex lens arranged opposite to said each photoelectric conversion pixel.

20. The electronic endoscope of claim 13 wherein said converging light device array is a conical lens array provided with a conical lens, as said each converging light device, having a larger section area than the area of said each photoelectric conversion pixel, said conical lens arranged opposite to said each photoelectric conversion pixel.

21. The electronic endoscope of claim 13 wherein said converging light device array is a conical reflecting lens array provided with a conical reflecting lens, as said each converging light device, having a larger aperture area than the area of said each photoelectric conversion pixel, said conical reflecting lens arranged opposite to said each photoelectric conversion pixel.

* * * * *